(12) United States Patent
Kawamura et al.

(10) Patent No.: US 9,125,928 B2
(45) Date of Patent: Sep. 8, 2015

(54) AGENT FOR SUPPRESSING THE FORMATION OF ABNORMAL SKIN CELLS CAUSED BY EXPOSURE TO LIGHT

(75) Inventors: Mitsuaki Kawamura, Osaka (JP); Shigeo Shinohara, Osaka (JP); Fumiki Harano, Osaka (JP); Akihiro Aoki, Osaka (JP); Eri Ueno, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/703,671

(22) PCT Filed: Jun. 24, 2011

(86) PCT No.: PCT/JP2011/065125
§ 371 (c)(1),
(2), (4) Date: Dec. 12, 2012

(87) PCT Pub. No.: WO2011/162416
PCT Pub. Date: Dec. 29, 2011

(65) Prior Publication Data
US 2013/0090301 A1  Apr. 11, 2013

(30) Foreign Application Priority Data

Jun. 25, 2010 (JP) ................................ 2010-145319

(51) Int. Cl.
| A01N 43/04 | (2006.01) |
| A61K 31/70 | (2006.01) |
| A61K 31/7076 | (2006.01) |
| A61K 9/00 | (2006.01) |
| A61K 47/10 | (2006.01) |

(52) U.S. Cl.
CPC ........... *A61K 31/7076* (2013.01); *A61K 9/0014* (2013.01); *A61K 47/10* (2013.01)

(58) Field of Classification Search
None
See application file for complete search history.

(56) References Cited

U.S. PATENT DOCUMENTS

| 3,978,213 A * | 8/1976 | Lapinet et al. ................. 514/47 |
| 4,702,913 A | 10/1987 | Marty |
| 4,814,171 A | 3/1989 | Marty |
| 2007/0135374 A1 | 6/2007 | Shinohara et al. |
| 2008/0260878 A1 | 10/2008 | Harano et al. |

FOREIGN PATENT DOCUMENTS

| JP | 60-214722 A | 10/1985 |
| JP | 9-157153 A | 6/1997 |
| JP | 2000-119155 A | 4/2000 |
| JP | 2001-521901 A | 11/2001 |
| JP | 2002-370986 A | 12/2002 |
| JP | 2003-516950 A | 5/2003 |
| JP | 2006-096730 A | 4/2006 |
| JP | 2006-206575 A | 8/2006 |
| JP | 2006-225271 A | 8/2006 |
| JP | 2007-161693 A | 6/2007 |
| JP | 2007-238588 A | 9/2007 |
| JP | 2009-227632 A | 8/2009 |
| WO | 90/00894 A1 | 2/1990 |
| WO | 99/22741 A1 | 5/1999 |
| WO | 01/43704 A1 | 6/2001 |
| WO | 2005/034902 A1 | 4/2005 |

OTHER PUBLICATIONS

Furukawa et al. Arch. Dermatol. Res. (2008), vol. 300, pp. 485-493.*
Database WPI Week 200844, Thomson Scientific, London, GB; AN 2008-G94096, XP000002659034.
Database WPI Week 200749, Thomson Scientific, London, GB; AN 2007-502522, XP000002659035.
Database WPI Week 200629, Thomson Scientific, London, GB; AN 2006-278538, XP000002659036.
Database WPI Week 200971, Thomson Scientific, London, GB; AN 2009-P41069, XP000002659037.
Gary L. Curtis et al., "Initiation-Promotion Skin Carcinogenesis: Inhibition by Cyclic and Non-Cyclic Nucleotides", Cancer Letters, 1979, pp. 291-300, vol. 6.
Eliezer Rapaport "Experimental Cancer Therapy in Mice by Adenine Nucleotides", Euro J. Cancer Clin. Oncol., 1988, pp. 1491-1497, vol. 24, No. 9.
International Search Report dated Sep. 29, 2011 for PCT/JP2011/065125.
Jacobson, et al. "Mapping the role of NAD metabolism in prevention and treatment of carcinogenesis," Molecular and Cellular Biochemistry, 1999, vol. 193, pp. 69-74.

* cited by examiner

Primary Examiner — Patrick Lewis
(74) Attorney, Agent, or Firm — Sughrue Mion, PLLC

(57) ABSTRACT

An object of the present invention is to provide an agent for suppressing the formation of skin cells induced by exposure to light such as ultraviolet light. The object is achieved by using a purine nucleic acid for suppressing the formation of abnormal skin cells caused by exposure to light.

10 Claims, 4 Drawing Sheets

VARIATION IN THE RELATIVE AMOUNT OF CPD (%)

AGENT FOR SUPPRESSING THE FORMATION OF ABNORMAL SKIN CELLS CAUSED BY EXPOSURE TO LIGHT

CROSS REFERENCE TO RELATED APPLICATIONS

This application is a National Stage of International Application No. PCT/JP2011/065125 filed Jun. 24, 2011, claiming priority based on Japanese Patent Application No. 2010-145319 filed Jun. 25, 2010, the contents of all of which are incorporated herein by reference in their entirety.

TECHNICAL FIELD

The present invention relates to an agent for suppressing the formation of abnormal skin cells caused by exposure to light.

BACKGROUND ART

In recent years, the effect of exposure to light such as sunlight irradiation on the skin is becoming a serious worldwide problem. In particular, in the United States, Europe, and Australia, the increase in incidence of skin cancer has become a serious problem. One of the factors of the increase in skin cancer is an ongoing increase in the amount of exposure to ultraviolet light in daily life due to the destruction of the ozone layer by chlorofluorocarbon. In today's world, it is impossible to avoid the risk of forming abnormal skin cells caused by exposure to light, specifically, the risk of photocarcinogenesis (i.e., skin cancer induced by exposure to light, such as ultraviolet light).

Conventionally, surgical treatment, chemotherapy, and radiation therapy are combined for the treatment of skin cancer. However, depending on the detection timing and the degree of symptoms of skin cancer, it is common that skin cancer may not be effectively treated, and that the treatment may create a considerable burden on daily life. These problems significantly degrade the quality of life (QOL) of individuals. Therefore, there has been a strong demand for the establishment of a method for preventing the occurrence of skin cancer.

Conventionally, the prevention of skin cancer caused by ultraviolet light is carried out by a known method in which the skin is protected from ultraviolet light using an externally applied drug containing an ultraviolet light-absorbing agent such as octyl methoxycinnamate, butyl methoxydibenzoylmethane, and benzophenone; and an ultraviolet light-scattering agent such as titanium oxide and zinc oxide.

However, while ultraviolet light-absorbing agents and ultraviolet light-scattering agents prevent exposure to ultraviolet light, these agents have been reported to have adverse effects, such as skin irritation. In other words, while these agents inhibit the formation of abnormal skin cells caused by exposure to light, these agents have the potential to cause disorders due to the contact stimulus and the like.

Further, such drugs containing the above ingredients must be applied to the skin before exposure to ultraviolet light, because the purpose is to prevent exposure of the skin to ultraviolet light. Accordingly, in the case of ultraviolet light-absorbing agents and ultraviolet light-scattering agents, the skin cannot be prevented from exposure to ultraviolet light if the user forgets to apply these agents to the skin or when these agents are removed from the skin by perspiration or the like, leading to induction of DNA damage. As a result, the risk of forming abnormal skin cells caused by exposure to light cannot be avoided.

Accordingly, if it is possible to inhibit the formation of abnormal cells in the skin tissue by an ingredient that does not adversely affect the skin, even when the skin is directly exposed to sunlight such as ultraviolet, it will be an effective preventive measure against the formation of abnormal skin cells, which cannot be achieved with ultraviolet light-absorbing agents or ultraviolet light-scattering agents. Under such circumstances, there is a strong demand for the development of a preventive agent capable of suppressing the formation of abnormal skin cells caused by exposure to light in the skin tissue, without causing skin irritation and the like.

Meanwhile, purine nucleic acids such as adenosine phosphates have the following effects: moisture retention and prevention or amelioration of wrinkles (see Patent Literature 1); prevention or amelioration of pigmentation (see Patent Literature 2); promotion of collagen production (see Patent Literature 3); and the like, and have been drawing attention as ingredients having cosmetically and pharmaceutically beneficial effects on the skin.

Further, there are known documents, regarding the anti-cancer effect of the purine nucleic acids, in which the suppression of growth of cancer cells induced by chemical substances is investigated (see Non-Patent Literature 1 and 2). However, these investigations did not actually confirm the effect of the purine nucleic acids on cancer cells caused by sunlight such as ultraviolet. The effect was merely investigated by administration into the abdominal cavity, which is not easily available to the user.

As described above, no investigation has been made on the relationship between photocarcinogenesis and external (dermal) application of the purine nucleic acids, and it is completely unknown how the purine nucleic acids affect the suppression of formation of abnormal skin cells caused by exposure to light, or the prevention or treatment of photocarcinogenesis when applied externally.

CITATION LIST

Patent Literature

PTL 1: Japanese Unexamined Patent Publication No. 2006-225271
PTL 2: Japanese Unexamined Patent Publication No. 2006-206575
PTL 3: WO 2005/34902

Non-Patent Literature

NPL 1: Cancer Letters 6 (1979) pp. 291-300
NPL 2: Euro. J. Cancer Clin. Oncol. Vol. 24 (1988) pp. 1491-1497

SUMMARY OF INVENTION

Technical Problem

An object of the present invention is to provide an agent for suppressing the formation of abnormal skin cells (specifically, the development of skin cancer) induced by exposure to light such as ultraviolet.

Solution to Problem

The present inventors conducted intensive studies in an attempt to achieve the above object, and found that purine nucleic acids such as adenosine phosphates can reduce DNA mutation in skin cells caused by exposure to light, and exert an effect of suppressing the formation of abnormal skin cells caused by exposure to light, specifically, an effect of preventing photocarcinogenesis, by inducing apoptosis in mutated cells; and that the purine nucleic acids can effectively inhibit or prevent the formation of abnormal skin cells caused by exposure to light, specifically, the development of skin cancer, when applied to the skin not only before but also after exposure to light. The present invention was completed through further studies based on the above findings.

Specifically, the present invention provides the inventions described below.

Item 1. A purine nucleic acid for use suppressing the formation of abnormal skin cells caused by exposure to light, wherein the purine nucleic acid is externally applied.

Item 2. The purine nucleic acid according to Item 1, which is at least one member selected from the group consisting of adenosine monophosphates and salts thereof.

Item 3. The purine nucleic acid according to any one of Items 1 or 2, wherein the suppression of the formation of abnormal skin cells is accompanied by DNA repair or suppression of DNA mutation.

Item 4. The purine nucleic acid according to any one of Items 1 to 3, wherein the suppression of the formation of abnormal skin cells is accompanied by induction of apoptosis.

Item 5. The purine nucleic acid according to any one of Items 1 to 4, wherein the suppression of the formation of abnormal skin cells is prevention of skin tumor.

Item 6. The purine nucleic acid according to Item 5, wherein the prevention of skin tumor is accompanied by suppression of the initiation of skin tumor.

Item 7. The purine nucleic acid according to Item 5 or 6, wherein the prevention of skin tumor is accompanied by suppression of the promotion of skin tumor.

Item 8. The purine nucleic acid according to any one of Items 5 to 7, wherein the prevention of skin tumor is aimed for the prevention of skin cancer.

Item 9. The purine nucleic acid according to any one of Items 1 to 8, wherein the purine nucleic acid is dermally applied in an amount of 0.01 to 10 mg per $cm^2$ skin area.

Item 10. The purine nucleic acid according to any one of Items 1 to 9, which is dermally applied at a frequency of 2 to 5 times a day.

Item 11. The purine nucleic acid according to any one of Items 1 to 10, wherein the light is UV-B.

Item 12. The purine nucleic acid according to any one of Items 1 to 11, wherein the purine nucleic acid is used by application to the skin before or after light irradiation.

Item 13. A composition used for suppressing the formation of abnormal skin cells caused by exposure to light, comprising a purine nucleic acid as an active ingredient.

Item 14. The composition according to Item 13, comprising at least one member selected from the group consisting of adenosine monophosphates and salts thereof in an amount of 0.5 to 20 wt % based on the total weight of the composition.

Item 15. The composition according to Item 13 or 14 as an externally applied drug, externally applied quasi-drug, or cosmetic product.

Item 16. A method for suppressing the formation of abnormal skin cells caused by exposure to light, comprising dermally applying an effective amount of purine nucleic acid to an area of skin where DNA mutation have developed or may develop due to exposure to light.

Item 17. A method for suppressing the formation of abnormal skin cells caused by exposure to light, comprising the steps of: dermally applying an effective amount of a purine nucleic acid to an area of skin that has been or may be exposed to light; and confirming that abnormal skin cells are not formed in the area of skin to which the purine nucleic acid has been dermally applied.

Item 18. Use of a purine nucleic acid for producing an agent for suppressing the formation of abnormal skin cells caused by exposure to light.

Advantageous Effects of Invention

According to the present invention, it is possible to reduce the amount of DNA mutants in skin cells generated by exposure to light, and effectively inhibit or prevent the formation of abnormal skin cells caused by exposure to light, specifically, photocarcinogenesis. Therefore, the present invention provides an effective preventive measure for reducing the risk of forming abnormal skin cells caused by exposure to light, specifically, the risk of developing skin cancer. Further, because the agent of the present invention for suppressing the formation of abnormal skin cells has an action of DNA repair and an action of suppressing mutation, the suppression or prevention of the formation of abnormal skin cells caused by exposure to light, such as photocarcinogenesis, can be expected when the agent is applied to the skin either before or after exposure to light. Accordingly, the regular use of the agent allows suppression or prevention of the formation of abnormal skin cells caused by exposure to light without essentially requiring the use of the agent before going outside, and without causing skin irritation.

DESCRIPTION OF EMBODIMENTS

Figure 1A:
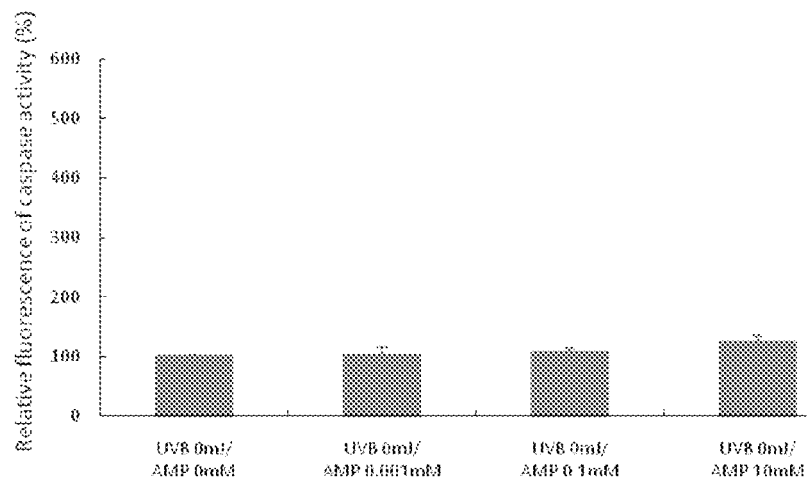
FIG. 1a shows results of evaluation of the effect of adenosine monophosphate on the caspase activity in normal human epidermal keratinocytes in Example 1.

In the present invention, purine nucleic acids are used for suppressing the formation of abnormal skin cells caused by exposure to light.

In other words, a purine nucleic acid is used as an agent for suppressing the formation of abnormal skin cells caused by exposure to light in the present invention. The agent is sometimes herein referred to as "the agent of the present invention".

Further, the composition of the present invention used for suppressing the formation of abnormal skin cells caused by exposure to light contains a purine nucleic acid as an active ingredient.

In the specification, examples of the formation of abnormal skin cells caused by exposure to light include skin tumor.

In the specification, the terms "suppression" and "prevention" as in the suppression and prevention of the formation of abnormal skin cells caused by exposure to light can be interpreted as having similar meaning.

Examples of the "suppression of the formation of abnormal skin cells caused by exposure to light" include "prevention of skin cancer."

In the specification, the term "accompanied by" means an occurrence of an event in association with another event. It does not matter which event is the cause or the result, and these events do not have to occur simultaneously.

In the present invention, the purine nucleic acid is the collective term for purine, various derivatives having a purine nucleus as a skeleton, and salts thereof. Examples of purine and various derivatives having a purine nucleus as a skeleton used as active ingredients in the present invention are not particularly limited, insofar as they are pharmaceutically or cosmetically acceptable. Specific examples thereof include adenine, guanine, deaminated compounds thereof (hypoxanthine and xanthine), adenosine, guanosine, inosine, adenosine phosphates (adenosine monophosphates such as adenosine 2'-monophosphate, adenosine 3'-monophosphate, and adenosine 5'-monophosphate; adenosine diphosphates such as adenosine 5'-diphosphate; and adenosine triphosphates such as adenosine 5'-triphosphate), guanosine phosphates (guanosine monophosphates such as guanosine 3'-monophosphate and guanosine 5'-monophosphate; guanosine diphosphates such as guanosine 5'-diphosphate; and guanosine triphosphates such as guanosine 5'-triphosphate), adenylosuccinate, xanthylic acid, inosinic acid, flavine adenine dinucleotide (FAD), nicotinamide adenine dinucleotide (NAD), and the like. Of these, examples of those having an excellent action of suppressing or preventing the formation of abnormal skin cells caused by exposure to light include, preferably, adenosine phosphates; more preferably, adenosine monophosphates; and particularly preferably, adenosine 5'-monophosphate (AMP).

Further, the salt form of purine nucleic acids is not particularly limited insofar as it is pharmaceutically or cosmetically acceptable. Specific examples thereof include alkali metal salts such as sodium salts and potassium salts; alkaline earth metal salts such as magnesium salts, calcium salts, and barium salts; basic amino acid salts such as arginine and lysine; ammonium and ammonium salts such as tricyclohexylammonium salt; and various alkanolamine salts such as monoethanolamine, diethanolamine, triethanolamine, monoisopropanolamine, diisopropanolamine, and triisopropanolamine. Of these, alkali metal salts are preferable, and sodium salts are further preferable.

These purine nucleic acids may be used alone, or in any combination of two or more as active ingredients of the agent for suppressing the formation of abnormal skin cells caused by exposure to light.

The content of purine nucleic acid in the composition of the present invention, which comprises a purine nucleic acid as an active ingredient and is used for suppressing the formation of abnormal skin cells caused by exposure to light, can be suitably determined according to the type of purine nucleic acids, form of the formulation, desired effect, and the like. Specifically, the content of purine nucleic acid in the composition is 0.5 to 20 wt %, preferably 0.5 to 10 wt %, more preferably 1 to 10 wt %, further preferably 1 to 7 wt %, and particularly preferably 2 to 5 wt %, based on the total weight of the composition. The formation of abnormal skin cells can be more effectively inhibited or prevented by satisfying the above content range.

The agent of the present invention for suppressing the formation of abnormal skin cells caused by exposure to light may be prepared in various forms by combining a pharmaceutically or cosmetically acceptable base or carrier, in addition to the purine nucleic acid. Any known base or carrier conventionally used in external preparations for the skin may be used as the pharmaceutically or cosmetically acceptable base and carrier.

Further, if necessary, various additives usable for external preparations for skin may be added to the agent of the present invention for suppressing the formation of abnormal skin cells caused by exposure to light. Examples of such additives include surfactants, coloring materials (dyes and pigments), flavoring materials, antiseptics, bactericides (antibacterials), thickeners, antioxidants, sequestering agents, cooling agents, deodorizers, humectants, ultraviolet light-absorbing agents, ultraviolet light-scattering agents, vitamins, plant extracts, astringents, anti-inflammatory agents (antiphlogistic agents), whiteners, cell activators, vasodilators, blood circulation accelerators, skin function accelerators, and the like.

The agent of the present invention for suppressing the formation of abnormal skin cells caused by exposure to light exerts a preventive action against the formation of abnormal skin cells caused by exposure to light when externally applied to an area of skin that has been or may be exposed to light such as ultraviolet light. Accordingly, the agent of the present invention for suppressing the formation of abnormal skin cells caused by exposure to light is prepared as an external preparation for the skin, which can be used on the daily basis, such as an externally applied drug, externally applied quasi-drug, or cosmetic product (e.g., skincare product).

The dosage form of the agent of the present invention for suppressing the formation of abnormal skin cells caused by exposure to light is not particularly limited insofar as it is applicable to the skin. Examples thereof include pastes, mousses, soft gels, liquids, emulsions, suspensions, creams, ointments, gels, sheets, aerosols, sprays, liniments, and the like. Of these dosage forms, liquids, emulsions, and gels are preferable. These dosage forms are prepared in accordance with a usual method in the relevant business field.

The agent of the present invention for suppressing the formation of abnormal skin cells caused by exposure to light is used specifically for the purpose of preventing skin tumor or skin cancer induced by exposure to light. In the present invention, the type of light that induces the formation of abnormal skin cells to be inhibited or prevented by the present invention is not particularly limited. Examples thereof include natural sunlight, ultraviolet light and radiation, with ultraviolet light being preferable, and UV-B being more preferable. Specifically, the agent of the present invention for suppressing the formation of abnormal skin cells caused by exposure to light is particularly suitably used for the prevention of photocarcinogenesis induced by exposure to ultraviolet light (particularly, UV-B) contained in sunlight.

Further, when the agent of the present invention for suppressing the formation of abnormal skin cells caused by exposure to light is used for the prevention of photocarcinogenesis, the type of skin cancer to be prevented by the present invention is not particularly limited insofar as it is induced in association with exposure to light. Specific examples thereof include malignant melanoma, basal cell carcinoma, and squamous cell carcinoma.

The agent of the present invention for suppressing the formation of abnormal skin cells caused by exposure to light is applied to an area of skin that has been or may be exposed to light. In other words, the agent of the present invention for suppressing the formation of abnormal skin cells caused by exposure to light may be applied to an area of skin that has been exposed to light, or applied to an area of skin that may be exposed to light before it is actually exposed to light.

When the agent of the present invention for suppressing the formation of abnormal skin cells caused by exposure to light is applied to the skin, the dosage and frequency thereof may be determined such that a suitable amount is applied to the skin once a day or at a frequency of 2 to 5 times a day, according to the type and concentration of purine nucleic acid, age and sex of the subject, applied area of skin, amount of light that the skin was or may be exposed to, and the like. Further, the dose of the agent of the present invention for suppressing the formation of abnormal skin cells caused by exposure to light may be set such that the amount of purine nucleic acid per $cm^2$ skin area is about 0.01 to 10 mg, preferably 0.1 to 5 mg.

As is clear from the above, the purine nucleic acid can prevent photocarcinogenesis. Accordingly, the agent of the present invention for suppressing the formation of abnormal skin cells caused by exposure to light can serve as an agent for preventing photocarcinogenesis. When the purine nucleic acid is used as an agent for preventing photocarcinogenesis, the type and concentration of the purine nucleic acid, other ingredients, dosage form, application site, application method, and the like are the same as described for the agent for suppressing the formation of abnormal skin cells caused by exposure to light.

The purine nucleic acid can induce apoptosis in skin cells that have become abnormal due to exposure to light. Accordingly, the agent of the present invention for suppressing the formation of abnormal skin cells caused by exposure to light can serve as an agent for inducing apoptosis in skin cells that have become abnormal due to exposure to light. When the purine nucleic acid is used as the agent for inducing apoptosis in skin cells that have become abnormal due to exposure to light, the type and concentration of the purine nucleic acid, other ingredients, dosage form, application site, application method, and the like are the same as described for the agent for suppressing the formation of abnormal skin cells caused by exposure to light.

The purine nucleic acid can inhibit the initiation of skin cancer. Accordingly, the agent of the present invention for suppressing the formation of abnormal skin cells caused by exposure to light can serve as an agent for suppressing the initiation of skin cancer. When the purine nucleic acid is used as the agent for suppressing the initiation of skin cancer, the type and concentration of the purine nucleic acid, other ingredients, dosage form, application site, application method, and the like are the same as described for the agent for suppressing the formation of abnormal skin cells caused by exposure to light.

The purine nucleic acid can inhibit the promotion of skin cancer. Accordingly, the agent of the present invention for suppressing the formation of abnormal skin cells caused by exposure to light can serve as an agent for suppressing the promotion of skin cancer. When the purine nucleic acid is used as the agent for suppressing the promotion of skin cancer, the type and concentration of the purine nucleic acid, other ingredients, dosage form, application site, application method, and the like are the same as described for the agent for suppressing the formation of abnormal skin cells caused by exposure to light.

Further, the purine nucleic acid can reduce the amount of mutated DNA in skin cells caused by exposure to light, and promote DNA repair. Accordingly, the agent of the present invention for suppressing the formation of abnormal skin cells caused by exposure to light can act in such a way as described above, and can serve as an agent for repairing DNA damage, suppressing DNA mutation, or reducing DNA mutation. When the purine nucleic acid is used as an agent for repairing DNA damage, suppressing DNA mutation, or reducing DNA mutations, the type and concentration of the purine nucleic acid, other ingredients, dosage form, application site, application method, and the like are the same as described for the agent for suppressing the formation of abnormal skin cells caused by exposure to light.

EXAMPLES

The present invention will be described below with reference to Test Examples and Examples. However, the present invention is not limited to these Examples. Note that, in the following Examples and the like, the numbers expressed in "%" that indicate the content are weight percent, unless otherwise indicated.

Example 1

Action of Inducing Apoptosis in Mutant Cells Caused by Ultraviolet Irradiation

The present Example examined a change in the caspase activity when human epidermal cells treated with disodium adenosine 5'-monophosphate (AMP2Na) were irradiated with ultraviolet light.

<Test Method>

Human epidermal keratinocytes (purchased from Kurabo Industries Ltd.) were precultured using EpiLife-KG2 culture medium (produced by Kurabo Industries Ltd.) in 10 cm collagen-coated petri dishes (produced by Asahi Glass Co., Ltd.), and seeded at a density of 30,000 cells/well into a collagen-coated 96-well microplate. After cultivation in the EpiLife-KG2 culture medium for 8 hours, the culture medium was replaced with EpiLife culture medium (produced by Kurabo Industries Ltd.), followed by cultivation for an additional 16 hours. Subsequently, the culture medium was replaced with AMP2Na-containing culture medium adjusted to various concentrations. After treatment with the medium for 2 hours, the cells were washed with PBS (phosphate buffered saline), and the washed cells were irradiated with 30 mJ/$cm^2$ of UV-B using an ultraviolet irradiation device (HN-400, produced by ABE RIKOSHA). EpiLife culture medium was added again, followed by cultivation for 6 hours. Subsequently, the activity of caspase 3 expressed in the cells were measured using a SensoLyte™ Rh110 Caspase 3 Assay Kit (produced by AnaSpec, Inc.). The cells that were not irradiated with UV-B nor treated with AMP2Na was used as a control group. Further, in order to examine influences that AMP2Na affect the caspase activity of normal cells, caspase activity of the cells that were not irradiated with UV-B but treated with AMP2Na was determined.

<Results>

Figure 1B:
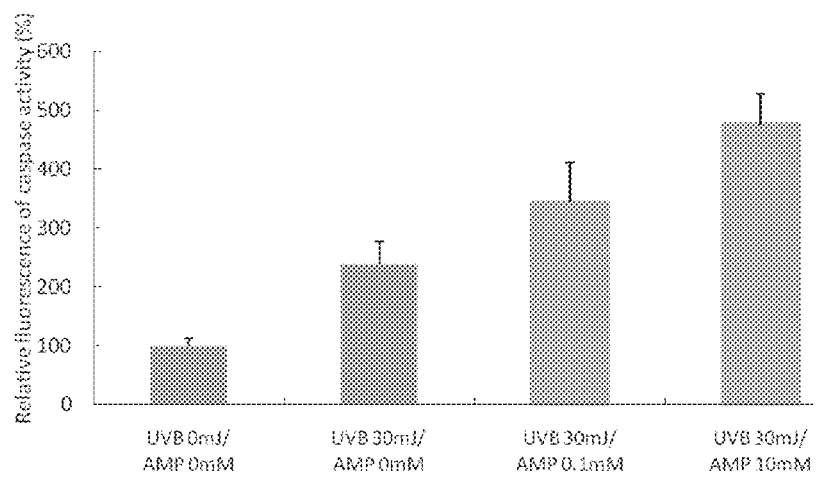
FIG. 1b shows results of evaluation of the effect of adenosine monophosphate on the caspase activity in ultraviolet-irradiated human epidermal keratinocytes in Example 1.

FIGS. 1a and 1b show the obtained results. It is clear from the results that while the non-ultraviolet-irradiated cells showed almost no increase in the caspase activity in spite of treatment with AMP2Na, the ultraviolet-irradiated cells showed a significant increase in the caspase activity with pretreatment of AMP2Na.

Caspase is a member of cysteine proteases that cause apoptosis in the cells. Caspase activity is generally regarded as an index for measuring the level of apoptosis activity.

Cells have a mechanism to trigger apoptosis on their own to kill themselves, as a biological defense mechanism against various stimuli that damage DNA, such as X-ray and ultraviolet. The present test also shows no change in caspase activity in the non-ultraviolet-irradiated cells regardless of whether the cells were treated with AMP2Na. This indicates that AMP2Na does not increase caspase activity and not induce apoptosis in normal cells. In contrast, it is clear from the increase of caspase activity that apoptosis was induced in the ultraviolet irradiated cells. Further, the present test shows a further increase of the activity in the cells treated with AMP2Na before ultraviolet irradiation, indicating that apoptosis was induced in mutant cells.

Example 2

Evaluation of the Action of Reducing DNA Mutation Induced by Ultraviolet Irradiation In this Example, normal mouse epidermal cells were irradiated with ultraviolet light, and then cultured in an AMP2Na-containing culture medium. Using the amount of cyclobutane pyrimidine dimers (CPD) as an index, the action of AMP2Na to reduce DNA mutation was examined.

<Test Method>

Normal mouse epidermal cell-derived JB6 cells (purchased from ATCC) were cultured in an FBS-containing MEM culture medium until subconfluent. Subsequently, $4 \times 10^5$ cultured cells were seeded into a 3.5 cm-dish with MEM (minimum essential medium) culture medium containing FBS (fetal bovine serum). Next day after the seeding, the culture medium was replaced with a serum-free MEM culture medium for serum starvation. Subsequently, the culture medium was replaced with PBS, followed by the irradiation with 15 mJ/cm$^2$ of UV-B. After ultraviolet irradiation, the culture medium was replaced with serum-free MEM culture medium containing 0.01 mM, 0.1 mM, or 1 mM AMP2Na or AMP2Na-free culture-medium (control). After the replacement of the culture medium, the cells were cultured with 5% $CO_2$ at 37° C. for 48 hours, and then collected.

Genomic DNA was extracted from the collected cells using a FastPure (trademark) DNA kit (Takara Bio Inc.). The extraction was carried out in accordance with the kit manual.

The amount of CPD in genomic DNA extracted from each cell was measured using ELISA. In particular, the extracted genomic DNA was heated at 100° C. for 10 minutes, and cooled on ice. Subsequently, genomic DNA was dispensed (50 μL/well) into a 96-well microplate coated with protamine sulfate, and dried. The following day, each of the wells was washed with PBS-T (PBS with Tween 20), and FBS-containing PBS was dispensed into each of the wells. The wells were then kept for 30 minutes at 37° C. Next, after washing with PBS-T, mouse anti-CPD antibody (purchased from Cosmo Bio Co., Ltd.) was dispensed into each of the wells, and the wells were then kept for 30 minutes at 37° C. After washing with PBS-T, biotin-labeled anti-mouse IgG (purchased from Southern Biotech) was dispensed into each of the wells, and the wells were then kept for 30 minutes at 37° C. After washing the wells, streptavidin-labeled horseradish peroxidase was dispensed into each of the wells, and the wells were then kept for 30 minutes at room temperature. Subsequently, the wells were washed with PBS-T and citrate phosphate buffer solution, and then citrate phosphate buffer solution containing hydrogen peroxide and o-phenylenediamine was dispensed into each of the wells. The wells were kept for 30 minutes at 37° C. for color development. Subsequently, 2 M sulfuric acid aqueous solution was added to the wells to terminate the color development reaction. Subsequently, the absorbance values at 492 nm were measured, and the amount of CPD in genomic DNA was calculated to determine the rate of change of CPD (variation in the relative amount of CPD; %) under each condition when the amount of CPD in the case of cultivation in the AMP2Na-free culture medium was assigned a value of 100%.

<Results>

Figure 2:
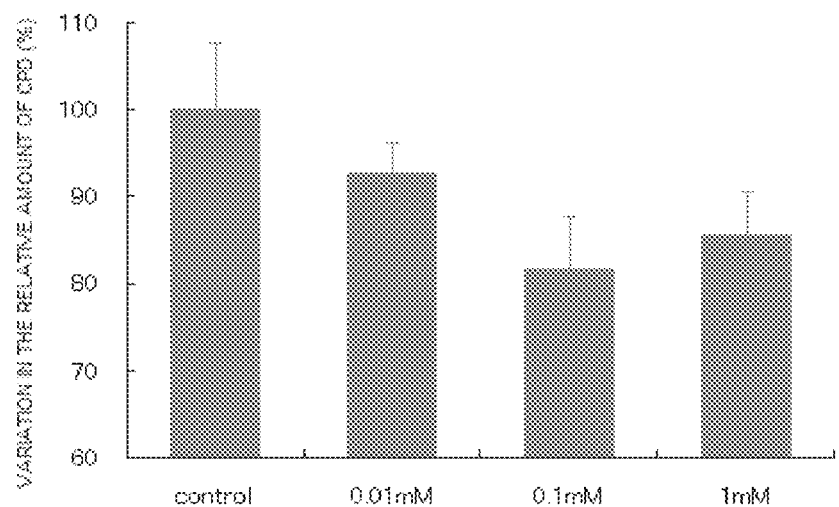
FIG. 2 shows results of evaluation of the effect of adenosine monophosphate on DNA mutation (CPD) in ultraviolet light-irradiated mouse epidermal keratinocyte in Example 2.

FIG. 2 shows the obtained results. The results show that the relative amount of CPD in the cells to which AMP2Na was added after ultraviolet irradiation decreased compared to the control group. The results therefore confirmed that AMP2Na decreases DNA mutation caused by ultraviolet irradiation. The results show that, when the cells were cultured in 0.1 mM and 1 mM AMP2Na-containing culture media, the decrease in the relative amount of CPD compared to the control group was significant, and DNA damage caused by ultraviolet irradiation was significantly suppressed. Based on the above, the above ingredient is expected to have the effect of preventing, in particular, the initiation of carcinogenesis.

Note that Example 1 is an in vitro test performed using the cells. In a practical application, taking into account individual differences, skin permeability, and penetrability into cells, consideration must taken for the adjustment of the concentration of AMP2Na to about 10 to 1,000 times more than the concentration of AMP2Na used in vitro, as described above.

Example 3

Evaluation of Preventive Effect on Skin Cancer in Ultraviolet Light-Irradiated Mice In this Example, hairless mice were irradiated with ultraviolet light, and the preventive effect of AMP2Na against photocarcinogenesis in the mice was examined.

<Test Method>

5-week-old female Hos:HR-1 mice were purchased from Japan SLC, Inc., and from the age of 7 weeks, ultraviolet light (UV-B) irradiation was performed on their back. The ultraviolet irradiation (irradiation amount per time: 60 mJ/cm$^2$) was performed once a day, 5 days a week, for 12 weeks.

Then, a 20% ethanol aqueous solution containing 3% of AMP2Na dissolved therein (test solution) and a 20% ethanol aqueous solution containing no AMP2Na (base) were prepared.

After feeding the ultraviolet light-irradiated mice under normal conditions for 1 week, the mice were divided into 3 groups (6 mice in each group) under the conditions shown in Table 1, and fed for 12 weeks.

TABLE 1

| | Test Conditions |
|---|---|
| Test solution-applied group | Test solution (0.1 mL) was applied to the entire back of the mice twice a day, 5 days a week, for 12 weeks of feeding. |
| Base-applied group | Base (0.1 mL) was applied to the entire back of the mice twice a day, 5 days a week, for 12 weeks of feeding. |

TABLE 1-continued

| Test Conditions | |
|---|---|
| Non-applied group | Mice were fed for 12 weeks without applying the test solution or base. |

<Results>

Figure 3:
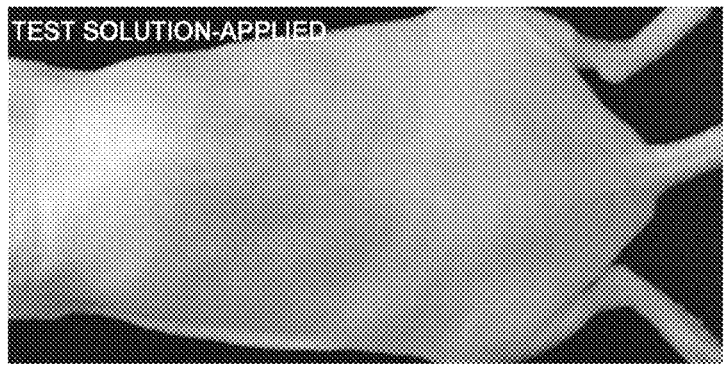
FIG. 3 shows results of images showing the back of the mice in each group in Example 3, in which the mice irradiated with ultraviolet light from the back were fed in separate groups: a test solution-applied group to which an ethanol aqueous solution containing adenosine monophosphate was applied; a base-applied group to which an ethanol aqueous solution was applied; and a non-applied group without any application.
Figure 3:
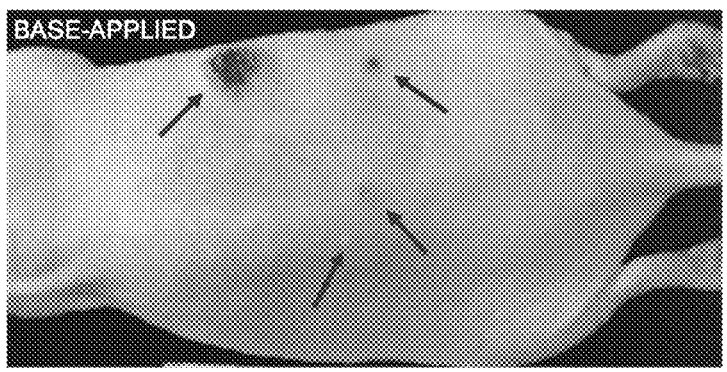
Figure 3:
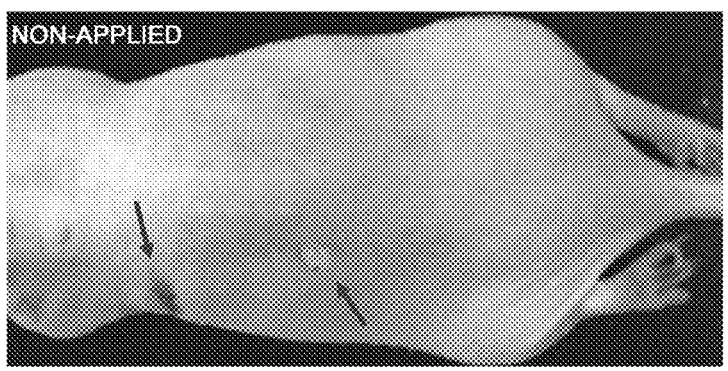
Figure 4:
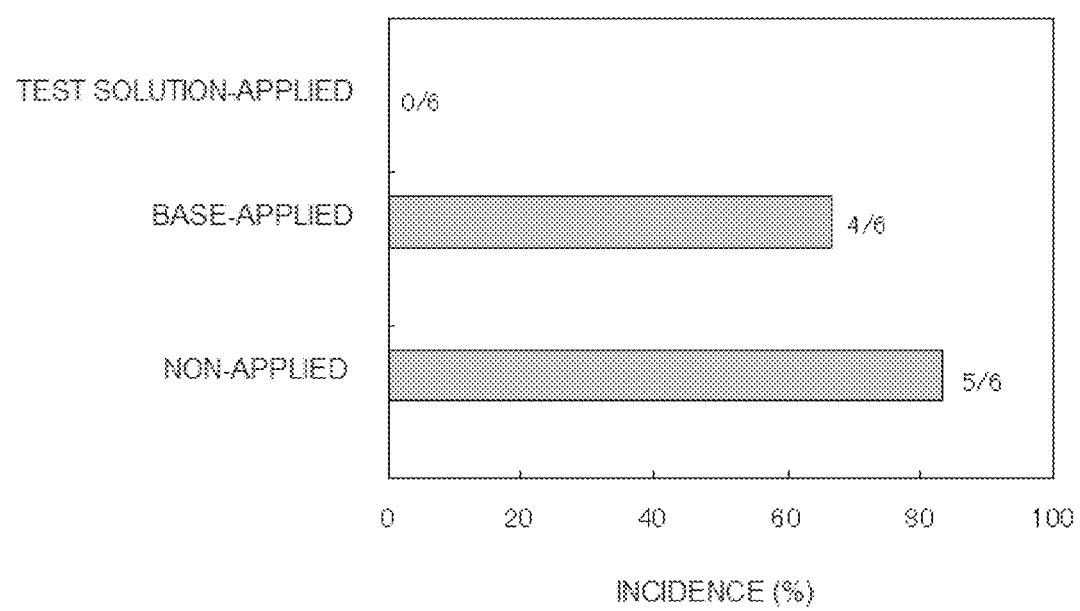
FIG. 4 shows results obtained by measuring the proportion of the population of the mice in which a tumor was observed (tumor incidence: %) in each group in Example 3, in which the mice irradiated with ultraviolet light from the back were fed in separate groups: a test solution-applied group to which an ethanol aqueous solution containing adenosine monophosphate was applied; a base-applied group to which an ethanol aqueous solution was applied; and a non-applied group without any application.

The skin conditions on the back of the mice in each group were observed at the 6th week from the start of the application of the test solution and the base. The development of tumors was determined, and the number of tumors was counted. FIG. 3 shows results of images of the back of the mice in each group, taken at the 6th week from the start of the application of the test solution or the base. FIG. 4 shows the proportion of the population of the mice in which a tumor was observed (tumor incidence: %) in each group at the 6th week from the start of the application of the test solution or the base.

As is clear from FIG. 3, tumor formation was observed on the back of the mice after ultraviolet irradiation in the base-applied group and the non-applied group, but not in the test solution-applied group. Further, as shown in FIG. 4, the tumor incidence after ultraviolet irradiation was 67% in the base-applied group and 83% in the non-applied group, whereas it was 0% in the test solution-applied group. It became clear that AMP2Na is capable of effectively preventing the occurrence of skin cancer induced by ultraviolet light.

Note that the average number of tumors developed per mouse in each group at the 6th week from the start of the application of the test solution or the base was as follows: 0 in the test solution-applied group; 2 in the base-applied group; and 1.8 in the non-applied group. These results also confirm that AMP2Na has an excellent preventive effect against skin cancer induced by ultraviolet light.

Further, the tumor incidence at the 12th week from the start of the application of the test solution or the base was 83% in the base-applied group, 100% in the non-applied group, and 17% in the test solution-applied group. This shows that AMP2Na has an action of strongly suppressing the development of tumors caused by ultraviolet irradiation. Accordingly, the ingredient is also expected to be effective in suppressing the promotion of carcinogenesis.

Prescription Example

A photocarcinogenesis-preventive agent in an emulsion form having the following composition is prepared.

| | |
|---|---|
| Adenosine monophosphate disodium | 3 (wt %) |
| Ethanol | 3 |
| Glycerin | 110 |
| Emulsifier, emulsifying assistant | 10 |
| Thickener | q.s. |
| Antiseptic, pH adjuster, flavoring materials | q.s. |
| Purified water | balance |
| Total | 100 wt % |

The invention claimed is:

1. A method for suppressing the formation of abnormal skin cells caused by exposure to UV-B, comprising dermally applying an effective amount of adenosine monophosphate and/or a salt thereof to an area of skin where DNA damage is induced by exposure to UV-B, and suppressing the formation of abnormal skin cells caused by exposure to UV-B.

2. The method according to claim 1, wherein the suppression of the formation of abnormal skin cells is accompanied by DNA repair or suppression of DNA mutation.

3. The method according to claim 1, wherein the suppression of the formation of abnormal skin cells is accompanied by induction of apoptosis.

4. The method according to claim 1, wherein the suppression of the formation of abnormal skin cells is prevention of skin tumors.

5. The method according to claim 4, wherein the prevention of skin tumors is accompanied by suppression of the initiation of tumors.

6. The method according to claim 4, wherein the prevention of skin tumors is aimed for the prevention of skin cancer.

7. The method according to claim 1, wherein the adenosine monophosphate and/or a salt thereof is applied in a form of a composition containing the adenosine monophosphate and/or a salt thereof as an active ingredient.

8. The method according to claim 7, wherein the adenosine monophosphate and/or a salt thereof is contained in an amount of 0.5 to 20 wt % based on the total weight of the composition.

9. A method for suppressing the formation of abnormal skin cells caused by exposure to UV-B, comprising dermally applying an effective amount of adenosine monophosphate and/or a salt thereof to an area of skin having been exposed to UV-B where DNA damage is induced to suppress the formation of abnormal skin cells caused by exposure to UV-B.

10. A method for suppressing the formation of abnormal skin cells caused by exposure to UV-B, comprising dermally applying an effective amount of adenosine monophosphate and/or a salt thereof to an area of skin having been exposed to UV-B where DNA damage is induced, and suppressing the formation of abnormal skin cells caused by exposure to UV-B.

* * * * *